United States Patent
Denissen

(10) Patent No.: US 9,430,717 B2
(45) Date of Patent: Aug. 30, 2016

(54) THREE DIMENSIONAL POLYLINE REGISTRATION USING SHAPE CONSTRAINTS

(71) Applicant: KONINKLIJKE PHILIPS N.V., Eindhoven (NL)

(72) Inventor: Sander Hans Denissen, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/428,743

(22) PCT Filed: Sep. 4, 2013

(86) PCT No.: PCT/IB2013/058282
§ 371 (c)(1),
(2) Date: Mar. 17, 2015

(87) PCT Pub. No.: WO2014/053925
PCT Pub. Date: Apr. 10, 2014

(65) Prior Publication Data
US 2015/0254526 A1    Sep. 10, 2015

Related U.S. Application Data

(60) Provisional application No. 61/708,206, filed on Oct. 1, 2012.

(51) Int. Cl.
*G06K 9/00* (2006.01)
*G06K 9/62* (2006.01)
*G06T 7/00* (2006.01)

(52) U.S. Cl.
CPC ........... *G06K 9/6214* (2013.01); *G06T 7/0051* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 8,077,943 B2* | 12/2011 | Williams | A61B 6/037 378/205 |
| 2002/0087101 A1 | 7/2002 | Barrick et al. | |
| 2008/0159606 A1* | 7/2008 | Suri | G06T 7/0083 382/128 |
| 2009/0137952 A1 | 5/2009 | Ramamurthy et al. | |
| 2010/0056904 A1 | 3/2010 | Saunders et al. | |
| 2014/0114180 A1 | 4/2014 | Jain | |
| 2014/0155737 A1 | 6/2014 | Manzke et al. | |

* cited by examiner

*Primary Examiner* — Weiwen Yang

(57) ABSTRACT

A system and method are provided for registering a coordinate system for a shape sensing system to a coordinate system for pre-procedural or intra-procedural imaging data. A stable curvature in a shape reconstruction is identified and matched to another curvature, where the other curvature is from another shape construction from a subsequent time or from imaging data from another imaging modality. The matched curvatures are aligned, aligning the coordinate systems for the respective curvatures.

15 Claims, 4 Drawing Sheets

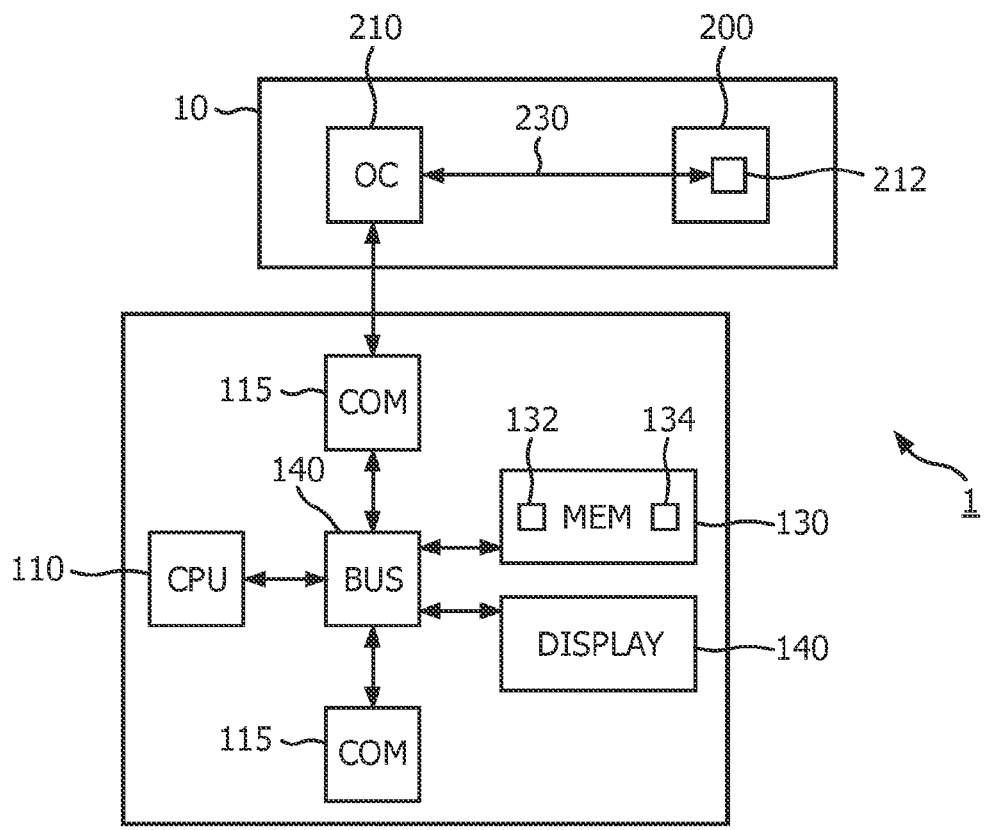
FIG. 1
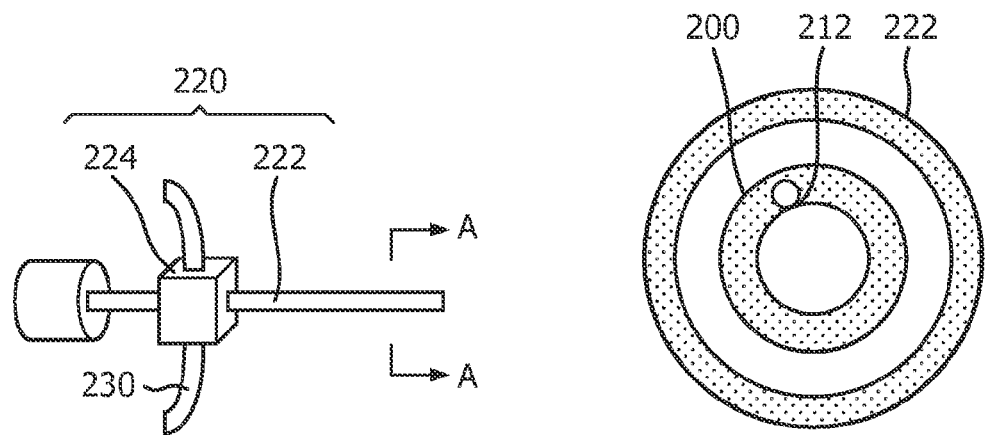
FIG. 2
FIG. 3

THREE DIMENSIONAL POLYLINE REGISTRATION USING SHAPE CONSTRAINTS

CROSS-REFERENCE TO PRIOR APPLICATIONS

This application is the U.S. National Phase application under 35 U.S.C. §371 of International Application Serial No. PCT/IB2013/058282, filed on Sep. 4, 2013, which claims the benefit of U.S. Application Ser. No. 61/708,206, filed on Oct. 1, 2012. These applications are hereby incorporated by reference herein.

FIELD OF THE INVENTION

The invention relates to the field of medical imaging and more particularly to three dimensional registration using shape matching.

BACKGROUND

Optical shape sensing technology provides a 3D shape of an optical fiber. By integrating such a fiber in interventional devices, the shape of the device can be known, up to a point very close to the tip of the device. However, knowing the shape alone is not enough: the shape must be placed in the context of (i.e., registered with) pre-procedural and/or intra-procedural imaging data. Having a correct (i.e., accurate) registration between the coordinate system of the shape sensing system and the coordinate system of the pre-procedural and/or intra-procedural imaging data is essential for the usage and adoption of the shape sensing technology.

In one application for shape sensing technology, a shape sensing optical fiber may be integrated into a tether attached to a surgical instrument and/or the instrument itself and used for instrument tracking. The fiber-optically tracked device is introduced endovascularly or endoluminally. To use the optical fiber for instrument tracking, an initial registration of the optical fiber coordinate system to a reference coordinate system is required. The reference coordinate system may be, for example, a 3D anatomical model derived from segmenting a Cone Beam Computer Tomography (CBCT) scan.

If an initial registration between a virtual device from the shape sensing fiber and pre-procedural or intra-procedural imaging data is used, misalignment may be caused by various effects. These effects include: inaccuracy of the shape reconstruction (even slight errors in shape reconstruction can cause significant misalignment), launch point movement (if the launch point of the shape sensing system moves during a procedure the entire shape will move causing misalignment), and patient movement (any movement by the patient following an initial registration will cause misalignment of the shape sensing coordinates and the image data coordinates).

One solution to misalignment caused after or during the initial registration is to reregister the coordinate systems based on x-ray imaging in real time. However, x-ray exposure should be limited due to its harmful effects. Also, x-ray only provides a 2D projection of a device, and the exact relation of the 2D projection and the fiber inside the device is not known, but can only be estimated.

SUMMARY

A system and method are provided for registering a coordinate system for a shape sensing system to a coordinate system for pre-procedural or intra procedural imaging data. According to one embodiment, three-dimensional shapes are detected in a shape sensing reconstruction which are identifiable by their curvature and are consistent over time, although not necessarily at the same position along the three dimensional shape. If two shapes over time or from different imaging sources have this same detectable curvature, their coordinate systems can be registered together in terms of translation and rotation by aligning the curvatures.

For purposes of this application, the terms shape and curve are used to describe a three dimensional curve from a shape reconstruction corresponding to the shape of a shape-sensing optical fiber disposed in or affixed to a surgical instrument. The term curvature is used to describe the form of a subsection of the three dimensional curve. The term bend is used to describe a non-straight curvature with single change or reversal of direction According to one aspect of the present invention, a system is provided for registering a coordinate system for a shape sensing system to a coordinate system for pre-procedural or intra procedural imaging data. The system comprises one or more surgical instruments incorporating an optical fiber with shape sensing sensors. An optical console is operably connected with the optical fiber and interrogates the optical shape sensors and determines the three-dimensional shape of the instrument from the return signals. A processor registers the coordinate system of the shape sensing fiber to a coordinate system of imaging data by matching a stable curvature in the optical fiber with a curvature from a different source and aligns the matched curvatures.

According to one embodiment the different source is a different imaging modality. According to one embodiment, the different imaging modality is a calculated image from pre-procedural or intra-procedural imaging data.

According to one embodiment, the processor is also the processor that processes the pre-procedural or intra-procedural imaging data.

According to one embodiment, the different source is a centerline from segmented pre-procedural or intra-procedural imaging.

According to one embodiment, the different source is a shape reconstruction from a different time.

According to one embodiment, the different source is a shape reconstruction from a different shape sensing fiber. For example, multi-tether tracking can be used for a shape sensed catheter and for a shape-sensed guidewire inside the catheter.

According to another aspect of the present invention, a method is provided for registering a coordinate system for a shape sensing system to a coordinate system for pre-procedural or intra procedural imaging data. A stable curvature is identified in a reconstructed image of a shape sensing fiber equipped instrument. The stable curvature is matched to a curvature from a different source. Then, the matched curvatures are aligned.

According to one embodiment, the stable curvature and the curvature from a different source are matched by comparing bend radii.

According to one embodiment, the stable curvature and the curvature from a different source are matched by comparing gradients of coordinates in the curvature.

According to one embodiment, the different source is a different imaging modality.

According to one embodiment, the different imaging modality is a calculated image from pre-procedural or intra-procedural imaging data.

According to one embodiment, the different source is a centerline from segmented pre-procedural or intra-procedural imaging.

According to one embodiment, the different source is a shape reconstruction from a different time.

According to one embodiment, more than one shape sensing fiber is used concurrently in a surgical procedure, and the different source is a shape reconstruction from a different shape sensing fiber.

According to one embodiment, the step of identifying a stable curvature comprises the steps of: measuring the radius of at least one bend in the shape of the reconstructed image of a shape sensing fiber equipped instrument; comparing a bend radius from a subsequent reconstructed image with the bend radius from the prior reconstructed image of a shape sensing fiber equipped instrument; determining whether the bend radii meet a predefined matching criteria; and saving the radius and location of the bend if the matching criteria is met.

According to another aspect of the present invention, a computer program product is provided for registering a coordinate system for a shape sensing system to a coordinate system for pre-procedural or intra procedural imaging data. The program product is encoded with: program instructions for identifying a stable curvature in a shape sensing fiber equipped instrument; program instructions for matching the stable curvature to a curvature from a different source; and program instructions for aligning the matched curvatures.

BRIEF DESCRIPTION OF THE DRAWINGS

The features and advantages of the invention will be more clearly understood from the following detailed description of the preferred embodiments when read in connection with the accompanying drawing. Included in the drawing are the following figures:

FIG. 1 is a block diagram of a system for registering a coordinate system for a shape sensing system to a coordinate system for pre-procedural or intra procedural imaging data by matching and aligning a stable shape from different sources according to an embodiment of the present invention;

FIG. 2 is a side view of an instrument and introducer from the system of FIG. 1 according to an embodiment of the present invention;

FIG. 3 is a sectional view of the instrument and introducer of FIG. 2 taken at section A-A in FIG. 2;

DETAILED DESCRIPTION

Figure 4:
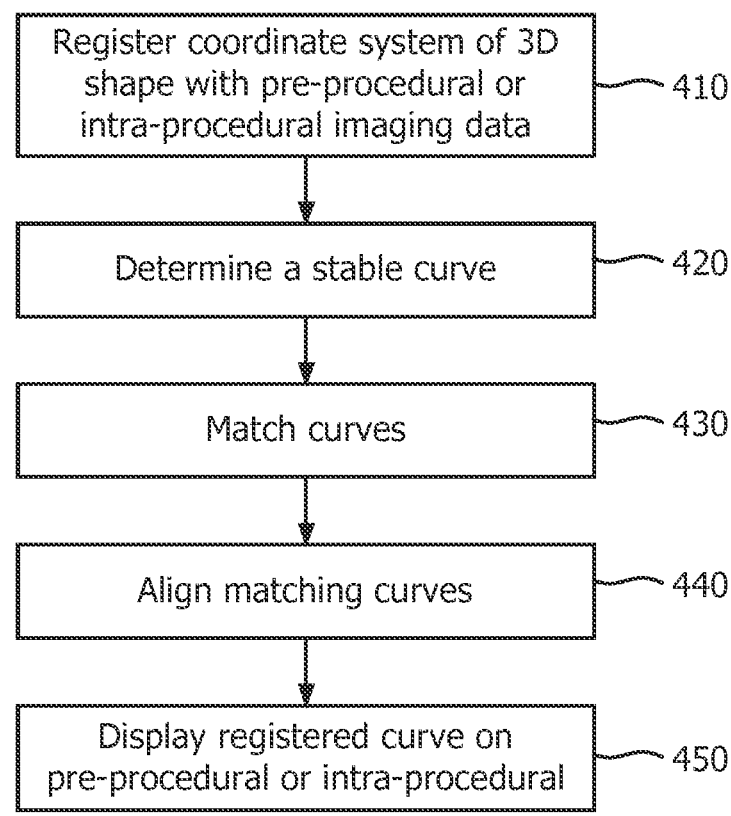
FIG. 4 is a flow diagram of a method for registering a coordinate system for a shape sensing system to a coordinate system for pre-procedural or intra procedural imaging data by matching and aligning a stable shape from different sources according to an embodiment of the present invention.

The present invention provides a method and system for registering a coordinate system for a shape sensing system to a coordinate system for pre-procedural or intra procedural imaging data by matching and aligning stable curvatures from different sources. The stability of the curvature is derived from physical constraints on a shape sensing fiber disposed in or affixed to a surgical instrument. The physical constraints may be provided, for example, by a rigid curved introducer sleeve, or anatomical structures which do not deform due to introduction of the instrument.

According to one embodiment, three-dimensional shapes are detected in a shape sensing reconstruction which are identifiable by their curvature and are consistent over time, although not necessarily at the same position along the three dimensional shape. If two shapes over time or from different imaging sources have this same detectable curvature, their coordinate systems can be registered together in terms of translation and rotation by aligning the curvatures.

FIG. 1 is a block diagram of an imaging system 1 that registers a coordinate system for a shape sensing system to a coordinate system for pre-procedural or intra procedural imaging data by matching and aligning a stable shape from different sources. According to one embodiment of the present invention, the imaging system 1 includes a shape sensing system 10 that is used in the registration of a shape sensing coordinate system to another coordinate system. The other coordinate system may be a coordinate system for pre-procedural or intra-procedural imaging data, for example.

The shape sensing system 10 comprises a shape sensing fiber 212 disposed in or affixed to a surgical instrument 200. The instrument 200 may be any instrument used during an intervention, including but not limited to: a mechanical scalpel (lancet), a laser scalpel, an endoscope, microscopic imaging probes, a surgical stapler, a retractor, a cautery device (electrical or optical), a catheter, a chisel, a clamp, a probe, a trocar, scissors, or the like. The instrument 200 may be manipulated by a physician to perform an intervention procedure. In many intervention procedures, a physician will use more than one instrument. Therefore, according to one embodiment, the shape sensing system 10 comprises more than one instrument 200.

The instrument 200 may be introduced endoluminally or endovascularly into a patient through an introducer 220, which may comprise one or more flexible and/or rigid sleeves, through which the instrument 200 may be advanced and/or retracted. According to one embodiment, shown in FIGS. 2 and 3, the instrument 200 is disposed in a flexible sleeve 222 which is disposed in a shorter rigid sleeve 224 used to introduce the instrument and flexible sleeve into a body lumen or vasculature.

The shape sensing fiber 212, together with an optical console 210, forms a shape sensing system 10 that provides strain information. The optical console 210 is operably connected to the shape sensing fiber 212. For example, the shape sensing fiber 212 may be connected to the optical console at an optical connector. The shape sensing fiber 212 is an optical fiber. A plurality of optical scatterers (e.g. Fiber Bragg Gratings or Rayleigh scatterers) may be distributed over the length of the optical fiber in the core or cladding to form sensors or gauges to measure strain. The optical console 210 interrogates the optical fiber, sending a broadband light signal along the optical fiber core and measuring the reflected wavelengths to determine length-resolved strain in the optical fiber core. Alternatively, the reflection spectrum may be obtained from a narrow band light source whereby the wavelength is swept in time. The strain data is then used to calculate the local curvature at each sensor, and the curvature data is compiled to calculate a three-dimensional shape of the shape sensing fiber 212, which corresponds to the shape of the instrument in which the shape sensing fiber is disposed or to which the shape sensing fiber is affixed. The optical console 210 may include a processor and may process the wavelength and strain data from the sensors. Alternatively, the optical console may send the wavelength or strain data to a processing system separate from the optical console for processing.

The imaging system 1 further comprises a processor 110, a memory 130 operably connected to the processor such as by a system bus 120 for example, and input/output (I/O) connectors 115 that operably connect the shape sensing system 10 to the processor 110. The processor 110 may be may be any device capable of executing program instructions, such as one or more microprocessors. Moreover, the processor 110 may be embodied in a general purpose computer.

The memory 130 may be any volatile or non-volatile memory device suitable for storing data and program instructions, such as a removable disc, a hard drive, a CD, a Random Access Memory (RAM), a Read Only Memory (ROM), or the like. Moreover, the memory 130 may comprise one or more memory devices.

The I/O connectors 115 may be any hardware that operably connects the processor 110 to the shape sensing system 210, another computer, or a data source. The I/O connectors may include, but are not limited to RS232 serial interface, Ethernet, and USB ports.

The processing system 100 further comprises an imaging program 132 stored on the memory 130 and executed by the processor 110 to receive and process imaging data the shape sensing system 10, and to display the images on a display 140. The imaging program 132 may include modules or units for various image processing functions.

The processing system 100 further comprises a registration program 134 stored on the memory 130 and executed by the processor 110 to register a coordinate system for the shape sensing system 10 to a coordinate system for pre-procedural or intra procedural imaging data. The imaging data may be stored imaging data or real-time imaging data from an MRI, X-ray, ultrasound, or any other type of imaging system appropriate for acquiring images of anatomic structures. According to one embodiment, the imaging system data comprises a three-dimensional image volume.

The registration program 134 may be a part of the imaging program 132, a standalone program, or a sub-routine callable by the imaging program.

The registration program 134 determines a stable curvature. Then, the registration program 134 matches a curvature from another source to the stable curvature, and aligns the matched curvatures. The other source may be data from the shape-sensing system 10 at a different time (temporal comparison). Alternatively, the other source may be imaging data from another imaging modality.

According to another embodiment, the other source may be a reconstruction from another shape sensing fiber disposed or affixed to a structure subject to the same shape constraints as the first shape sensing fiber. For example, one shape sensing fiber may be disposed in or affixed to an instrument such as a catheter, and another shape sensing fiber may be incorporated in a guidewire inside the catheter and therefore subject to the same shape constraints.

FIG. 4 is a flow diagram of a method for registering a coordinate system for a shape sensing system to a coordinate system for pre-procedural or intra procedural imaging data by matching and aligning a stable curvature from different sources according to an embodiment of the present invention.

According to one embodiment, the registration program 134 performs an initial alignment of the coordinate system of the shape sensing system 10 to a coordinate system from pre-procedural or intra-procedural imaging data (Step 410). The initial registration may be performed using any of a variety of known methods. For example, the initial registration may be performed by touching the shape sensing enabled instrument to a fiducial or an anatomical landmark corresponding to identifiable points in the imaging data.

Figure 5:
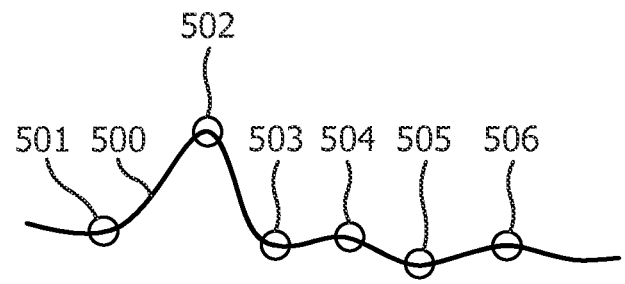
FIG. 5 is a view of a polyline curve showing various bends in a shape sensing fiber.

The registration program 134 determines a stable curvature (step 420). To determine a stable curvature, the registration program first identifies a curve in the shape sensing fiber 212. The shape sensing fiber 212 provides a polyline curve 500, as shown in FIG. 5. The polyline curve is a curve formed by multiple points (corresponding to the sensor locations) with each point subsequent on the shape sensing fiber 212 to the previous point.

The step of determining a stable curvature 420 is shown in more detail in FIG. 5. The registration program 134 identifies bends 501-506 in the polyline curve 500 (Step 421). To identify bends the registration program determines bend radii of the polyline curve 500. The bend radii may be determined by checking the rate and direction of curvature along the points of the polyline curve 500. The rate and direction of curvature may be determined from the strain data, for example. Alternatively, the registration program 134 may determine the bend radii by taking three points on the polyline curve at a predetermined spacing or sample rate, and calculating the distance from the middle point to the vector from the first point to the last point as a measure of curvedness.

According to another embodiment, the curvatures may be determined by calculating a gradient from coordinates on the polyline curve.

The registration program 134 compares curvatures temporally (i.e., over subsequent shape reconstructions) to check that a bend is stable (Step 422). For clinical purposes, a bend as distally located along the shape as possible is preferred, because the displacement of tip of the instrument with respect to the bend will be minimized. If the distance from the origin of the shape to a stable physical constraint on the instrument (and shape sensing fiber) is known, for example by using a curved introducer, the search window for bend radii can be limited to positions at the geodesic distance for the known stable physical constraint.

The registration program determines whether or not the curvature or bend is stable (Step 425). If the bend radii from subsequent shape reconstructions match within a predetermined margin of error the curvature is determined to be stable (Y branch from step 4125). If the curvature is not stable (N branch from step 425) additional bends are tested (Step 421).

Returning to FIG. 4, once a stable curvature is determined (Step 420), curvatures are matched to the stable curvature from another source (Step 430). The other source may be another shape reconstruction from a different time. Alternatively, the other source may be data from pre-procedural or intra-procedural imaging, such as an anatomical volume reconstruction from computer tomography. In another embodiment the other source may be a different shape sensing fiber subject to the same shape constraint as the first shape sensing fiber.

Figure 6:
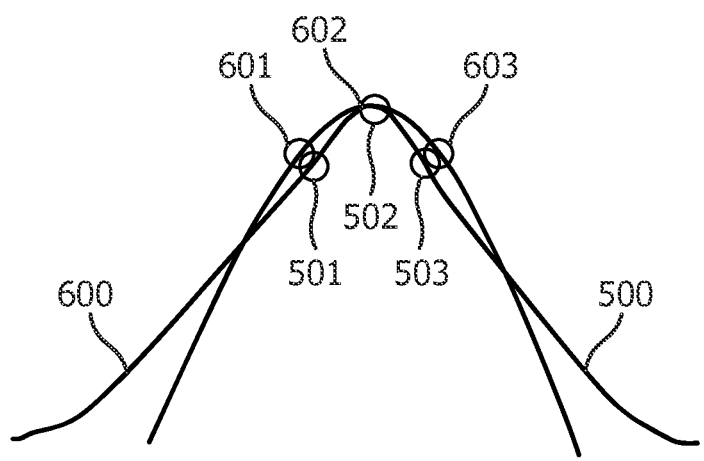
FIG. 6 shows a step of aligning matching curves according to an embodiment of the present invention.
Figure 7:
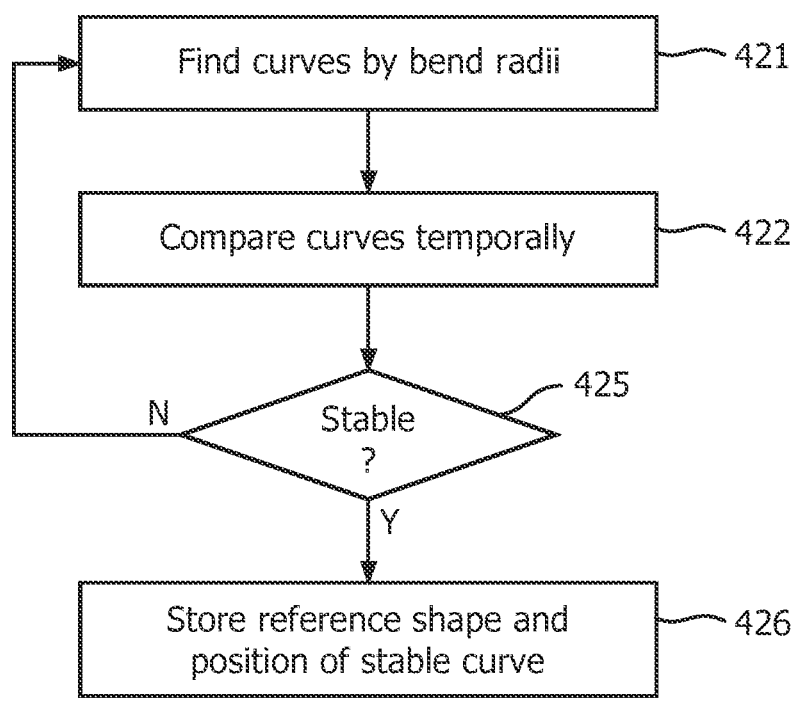
FIG. 7 is a flow diagram of a method for determining a stable curve according to an embodiment of the present invention.

The curvatures are matched by comparing the bend radii from the different curvatures of different curves as shown in FIG. 6. The bend radius of the curve 500 (stored from step 420) defined by points 501, 502, 503 is matched to the bend radius of curve 600 (from a different source) defined by points 610, 602, 603. If the bend radii match within a predetermined margin of error, then the curvatures are determined to match. Because the points lie at discrete distances, the curve of the new shape may have shifted between positions of the reference shape. According to various embodiments, a very small sample rate may be used or interpolation may be performed with Hermite curves or splines to improve detection.

The registration program 134 aligns the matching curvatures (Step 440). A translation and rotation are calculated to bring the tree-dimensional curvature from the different source with matching bend radius into alignment with the three-dimensional curvature from the stored stable curvature. The translation and rotation needed for alignment may be expressed in the form of a transformation matrix, which may be applied to the shape reconstruction to align it to the imaging data. The matrix may be calculated from coordinates of points on the matching curvatures.

According to one embodiment, the registration program 134 aligns the curvatures by taking the three points (bend point, proximal point, and distal point) from each curvature to form triangles which lie in the planes of the respective bends, then aligning the triangles.

According to one embodiment, the registration program 134 displays the shape reconstruction for the newly registered curvature on a pre-procedural or an intra-procedural image construction consistent with the registration (Step 450).

The invention can take the form of an entirely hardware embodiment or an embodiment containing both hardware and software elements. In an exemplary embodiment, the invention is implemented in software, which includes but is not limited to firmware, resident software, microcode, etc.

Furthermore, the invention may take the form of a computer program product accessible from a computer-usable or computer-readable storage device providing program code for use by or in connection with a computer or any instruction execution system or device. For the purposes of this description, a computer-usable or computer readable storage device may be any apparatus that can contain or store the program for use by or in connection with the instruction execution system, apparatus, or device.

The foregoing method may be realized by a program product comprising a machine readable storage device having a machine-executable program of instructions encoded thereon in a non-transitory computer readable medium, which when executed by a machine, such as a computer, performs the steps of the method. This program product may be stored on any of a variety of known machine-readable storage devices, including but not limited to compact discs, floppy discs, USB memory devices, and the like.

The storage device can be an electronic, magnetic, optical, electromagnetic, infrared, or semiconductor system (or apparatus or device). Examples of a computer-readable storage device include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain features are recited in mutually different claims does not indicate that a combination of these features cannot be used to advantage. Any reference signs in the claims should not be construed as limiting the scope of the invention.

What is claimed is:

1. A system for registering a coordinate system for a shape sensing system to a coordinate system for pre-procedural or intra procedural imaging data, comprising:
    at least one instrument incorporating an optical fiber having shape sensing sensors;
    an optical console that interrogates the optical shape sensors; and determines the three-dimensional shape of the instrument; and
    a processor that registers the coordinate system of the shape sensing fiber to a coordinate system of imaging data;
    characterized in the processor coordinate system of the shape sensing fiber to the coordinate system of imaging data by identifying a stable curvature in the optical fiber and matching the stable curvature in the optical fiber with a curvature from a different source and aligning the matched curvatures.

2. The system of claim 1, wherein the different source is a different imaging modality.

3. The system of claim 2, wherein the different imaging modality is a calculated image from pre-procedural or intra-procedural imaging data.

4. The system of claim 3, wherein the processor is also the processor that processes the pre-procedural or intra-procedural imaging data.

5. The system of claim 3, wherein the different source is a centerline from segmented pre-procedural or intra-procedural imaging.

6. The system of claim 1, wherein the different source is a shape reconstruction from a different time.

7. The system of claim 1, wherein the different source is a shape reconstruction from a different shape sensing fiber.

8. A method for registering a coordinate system for a shape sensing system to a coordinate system for pre-procedural or intra procedural imaging data, characterized in the processor:
    identifying a stable curvature in a reconstructed image of a shape sensing fiber equipped instrument;
    matching the stable curvature to a curvature from a different source; and
    aligning the matched curvatures.

9. The method of claim 8, wherein the stable curvature and the curvature from a different source are matched by comparing bend radii.

10. The method of claim 8, wherein the stable curvature and the curvature from a different source are matched by comparing gradients of coordinates in the curvature.

11. The method of claim 8, wherein the step of identifying a stable curve comprises the steps of:
    measuring the radius of at least one bend in the curve of the reconstructed image of a shape sensing fiber equipped instrument;

comparing the measured bend radius with a prior reconstructed image of a shape sensing fiber equipped instrument;

determining whether the bend radii meet a predefined matching criteria; and saving the radius and location of the bend if the matching criteria is met.

12. The method of claim 8, wherein the different source is a shape reconstruction from a different shape sensing fiber.

13. The method of claim 8, wherein the different source is a different imaging modality.

14. The method of claim 13 wherein the different imaging modality is a calculated image from pre-procedural or intra-procedural imaging data.

15. A computer program product for registering a coordinate system for a shape sensing system to a coordinate system for pre-procedural or intra procedural imaging data, comprising a computer-readable storage device having encoded thereon on a non-transitory computer readable medium, a computer-executable program of instruction, the program instruction characterized in:

program instructions for identifying a stable curvature in a shape sensing fiber equipped instrument;

program instructions for matching the stable curvature to a curvature from a different source; and program instructions for aligning the matched curvatures.

* * * * *